(12) United States Patent  
Yoshizawa et al.

(10) Patent No.: US 7,280,231 B2  
(45) Date of Patent: Oct. 9, 2007

(54) APPARATUS FOR DETERMINING WALL THICKNESS OF MICROCAPSULE

(75) Inventors: Hidekazu Yoshizawa, Okayama (JP); Masaki Hayashi, Okayama (JP)

(73) Assignee: Daicel Chemical Industries, Ltd., Sakai-Shi (JP)

( * ) Notice: Subject to any disclaimer, the term of this patent is extended or adjusted under 35 U.S.C. 154(b) by 338 days.

(21) Appl. No.: 10/792,869

(22) Filed: Mar. 5, 2004

(65) Prior Publication Data

US 2004/0190009 A1    Sep. 30, 2004

(30) Foreign Application Priority Data

Mar. 27, 2003    (JP) ............... 2003/087912

(51) Int. Cl.  
*G01B 11/28* (2006.01)
(52) U.S. Cl. .................................. 356/630
(58) Field of Classification Search ........ 356/630–632, 356/73.1, 338, 336, 343  
See application file for complete search history.

(56) References Cited

U.S. PATENT DOCUMENTS 4,565,449 A * 1/1986 Grego .................. 356/484

6,538,755 B1 * 3/2003 Propst, Jr. .............. 356/635  
6,919,954 B2 * 7/2005 Sasaki et al. ............ 356/128

OTHER PUBLICATIONS

Toshiaki Dobashi et al., *Langmuir*, vol. 14, (1998), pp. 745-749.

* cited by examiner

*Primary Examiner*—Gregory J. Toatley, Jr.  
*Assistant Examiner*—Isiaka O Akanbi  
(74) *Attorney, Agent, or Firm*—Birch, Stewart, Kolasch & Birch, LLP

(57) ABSTRACT

A thickness-determining apparatus for determining a wall thickness of a microcapsule having a refractive index n1 comprises a sensor 1 for detecting a light scattering intensity data I1 with respect to the microcapsule dispersed in a medium having a refractive index n1, and a light scattering intensity data I2 with respect to the microcapsule dispersed in a medium having a refractive index n2; a memory circuit 3 for storing a theoretical equation correlating a light scattering intensity characteristic with a particle size; and an arithmetic circuit 5 for calculating an inner diameter r1 and an outer diameter r2 from the theoretical equation based on the light scattering intensity data I1 and I2, and calculating the wall thickness.

6 Claims, 2 Drawing Sheets

US 7,280,231 B2

APPARATUS FOR DETERMINING WALL THICKNESS OF MICROCAPSULE

This Nonprovisional application claims priority under 35 U.S.C. § 119(a) on Patent Application No(s). 087912/2003 filed in Japan on Mar. 27, 2003, the entire contents of which are hereby incorporated by reference.

BACKGROUND OF THE INVENTION

1. Field of the Invention

The present invention relates to an apparatus for determining a wall (or shell) thickness of a microcapsule nondestructively and conveniently by light-scattering techniques, and a method for the same.

2. Description of the Related Art

As a method for determining (or measuring) a wall thickness of a microcapsule, there have been known a method which comprises enveloping and embedding or solidifying a microcapsule with an epoxy resin, paste, or the like, then breaking the microcapsule, and observing the broken-out section of the solidified matter by a scanning electron microscope (SEM) to measure the wall thickness with the eye, and a method which comprises cutting a microcapsule by a microtome to give an ultrathin section, and observing the cross section of the ultrathin section by a transmission electron microscope (TEM) or an optical microscope (OM) to measure the wall thickness with the eye.

However, these methods have some problems as follows: (i) since the microcapsule is very small in size, it is difficult to break the enveloped and embedded microcapsule certainly; (ii) in cutting, if the capsule wall is hard, the wall is often broken or crushed, and if the capsule wall is soft, the wall is often deformed; (iii) it is necessary to dry the microcapsule for breaking or cutting since the microcapsule is usually formed in an aqueous phase or an oil phase, however, the capsule wall is deformed by dryness; (iv) even when the microcapsule is breakable, the capsule involving a liquid therein has possibilities that the liquid vaporization adversely affects the electron gun in SEM or TEM observation; and (v) since the thickness observed by the microscope is only based on a local field of view, it is difficult to obtain a statistical information on the basis of a wide field of view. These methods therefore not only need accurate and complicated operations such as breaking or cutting but also find difficulty obtaining a reliable data adapted to meet the actual situation. Furthermore, it is extremely difficult to measure a thickness for a polydisperse microcapsule statistically.

Meanwhile, it is known to analyze a structure of a microcapsule by light scattering techniques. In the light scattering techniques, a microcapsule can be analyzed without destruction. In the ordinary light scattering techniques, the outer diameter of the microcapsule can be determined, but the capsule wall thickness cannot be determined.

Dobashi et al. derived a capsule wall thickness by irradiating a single microcapsule with a light, and conducting a fitting analysis to a dependency of a scattering angle on the resultant scattered light intensity on the basis of Mie Scattering Theory (Dobashi et al., Langmuir Vol. 14, pp. 745 to 749 (1998)). However, since this method utilizes a complicated theoretical equation (scattering function) in which the inner diameter and the outer diameter are the variables, complicated operations are required and the fitting analysis sometimes becomes difficult depending on the wall thickness of the capsule, or others. Moreover, in this method, it is extremely complicated to derive the wall thickness of a large number of microcapsules having a particle size distribution even if it is possible, and it is difficult to calculate the thickness adapted to meet the actual situation.

SUMMARY OF THE INVENTION

The present invention provides an apparatus for determining a wall (or shell)=thickness of a microcapsule without destruction conveniently and certainly, and a method for the same.

The present invention also provides an apparatus for determining a wall thickness of a microcapsule with a high degree of accuracy even a polydisperse microcapsule, and a method for the same.

The inventors of the present invention made intensive studies to achieve the above objects and finally found that the inner diameter of a microcapsule can be quasi-determined as the outer diameter by corresponding a refractive index of a medium with that of a wall of the microcapsule in a light scattering intensity measurement of the microcapsule in the medium. The present invention was accomplished based on the above findings.

That is, the present invention includes an apparatus for determining a wall thickness of a microcapsule whose wall has a refractive index $n_1$, which comprises: (i) detecting means for detecting a light scattering intensity data $I_1$ with respect to the microcapsule dispersed in a medium having a refractive index $n_1$, and a light scattering intensity data $I_2$ with respect to the microcapsule dispersed in a medium having a refractive index $n_2$, (ii) memory means for storing a theoretical equation for correlating a characteristic of a light scattering intensity with a particle size, and (iii) computing means for calculating an inner diameter $r_1$ and an outer diameter $r_2$ of the wall, from the theoretical equation based on the light scattering intensity data $I_1$ and $I_2$, and calculating a wall thickness ($r_2-r_1$). The characteristic of the light scattering intensity may be an intensity characteristic depending on a scattering angle (i.e., the characteristic may be represented by a relational expression between a light scattering intensity and a scattering angle). Moreover, in the apparatus, a distribution $P(r_1)$ of the inner diameter and a distribution $P(r_2)$ of the outer diameter may be calculated based on the light scattering intensity data $I_1$ and $I_2$ for a polydisperse microcapsule, and a wall thickness distribution $P(r_2-r_1)$ is calculated. The apparatus ensures determination (or calculation) of a wall thickness of a microcapsule even in a relatively thin wall. Incidentally, the difference between the refractive index $n_1$ and the refractive index $n_2$ may be about 0.01 to 0.5.

The present invention also includes a method for determining a wall thickness of a microcapsule having a wall of a refractive index $n_1$, which comprises: (i) measuring a light scattering characteristic for the microcapsule dispersed in a medium having a refractive index $n_1$ to provide a light scattering intensity data $I_1$ followed by calculating an inner diameter $r_1$ of the wall, and (ii) measuring a light scattering characteristic for the microcapsule dispersed in a medium having a refractive index $n_2$ to provide a light scattering intensity data $I_2$ followed by calculating an outer diameter $r_2$ of the wall, for calculating the wall thickness ($r_2-r_1$).

According to such an apparatus and method, the inner diameter of the microcapsule can be determined as the outer diameter with the use of a difference in refractive index between the core of the microcapsule and the wall thereof by measuring a light scattering intensity characteristic in the medium having a refractive index $n_1$. Moreover, the outer diameter of the microcapsule can be determined by measuring a light scattering intensity characteristic in the medium having a refractive index n2. From these results, the thickness of the microcapsule can be calculated.

DETAILED DESCRIPTION OF THE INVENTION

Figure 1:
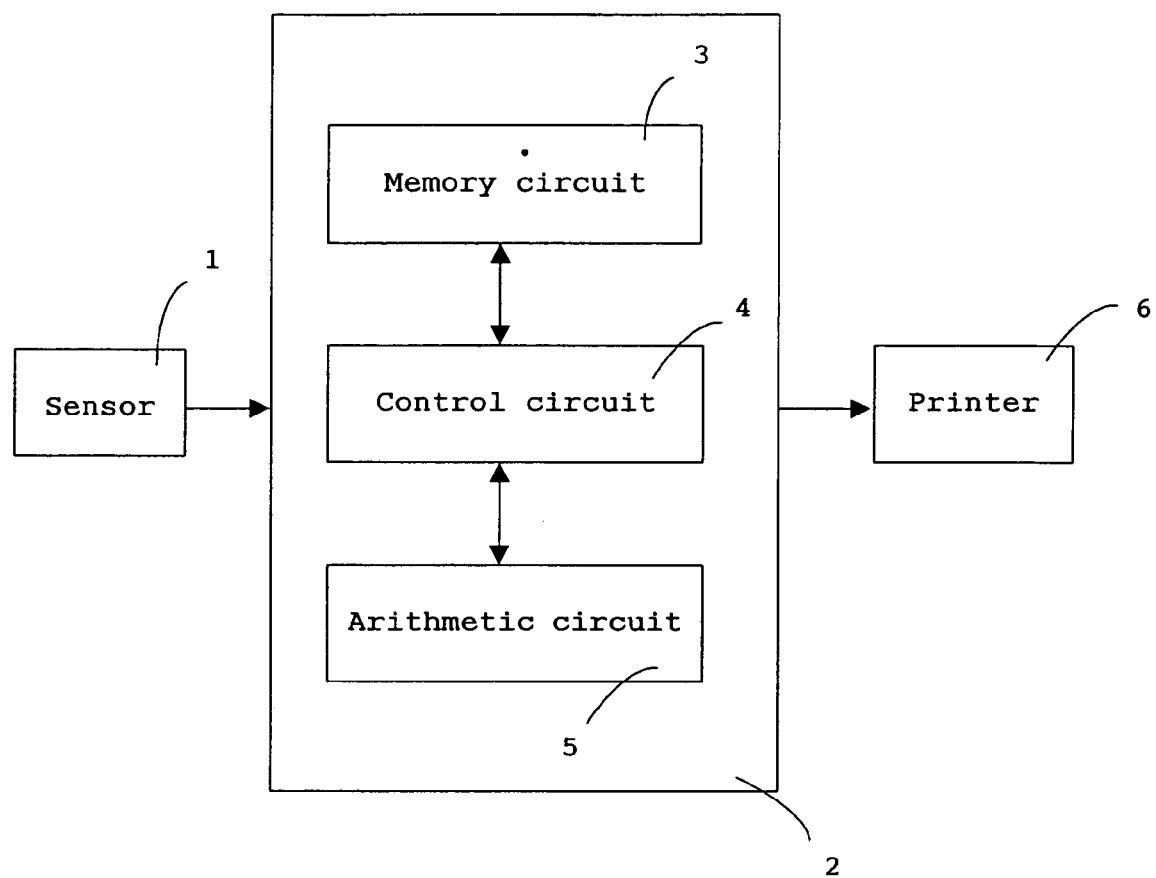
FIG. 1 is a block diagram showing an embodiment of the apparatus of the present invention.
Figure 2:
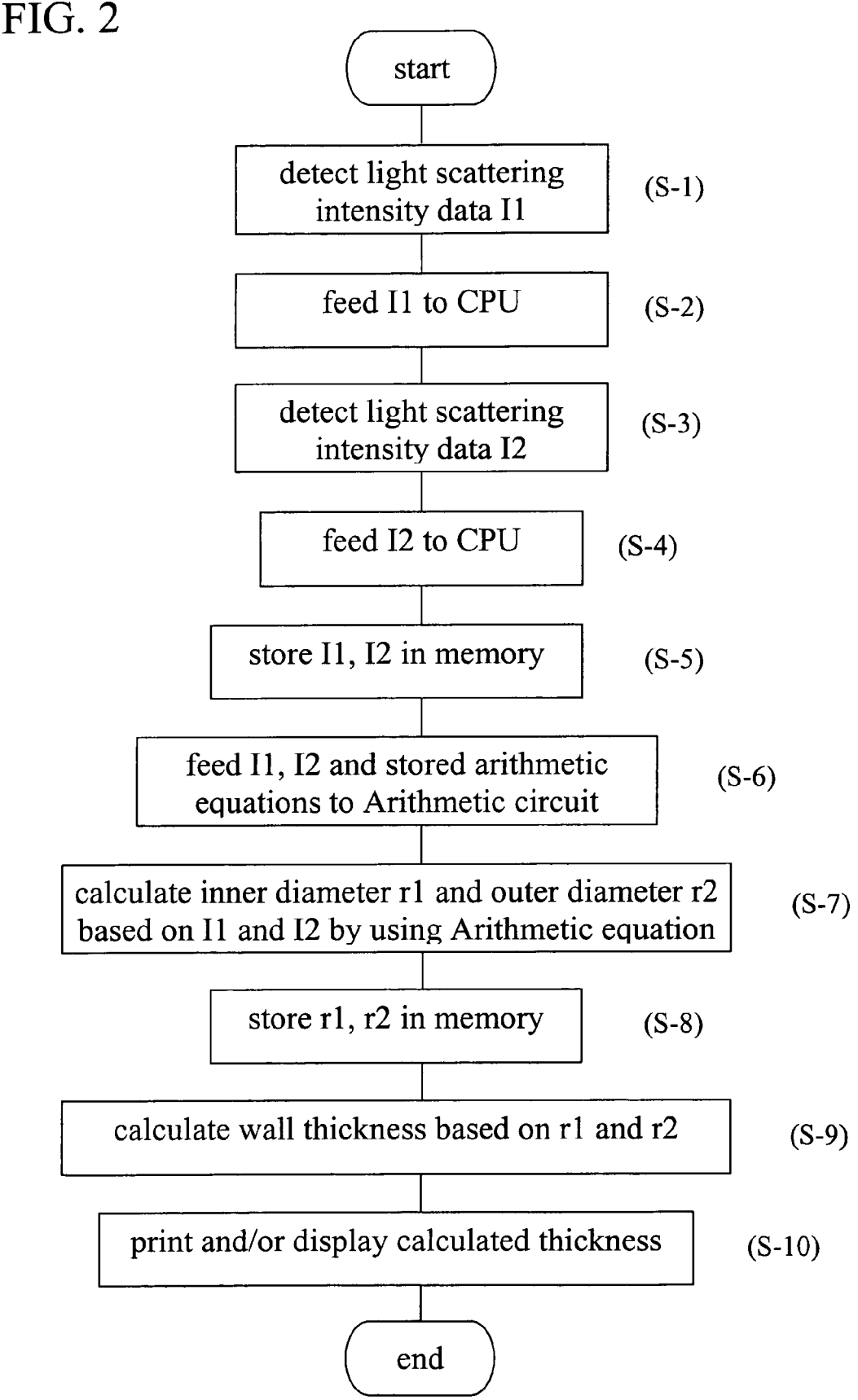
FIG. 2 is a flowchart that shows an operation of the apparatus shown in FIG. 1.

The present invention shall now be described in detail with reference if necessary to the attached drawings. FIG. 1 is a block diagram showing an embodiment of the apparatus of the present invention, and FIG. 2 is a flowchart that shows an operation of the apparatus shown in FIG. 1.

The thickness-determining apparatus shown in FIG. 1 comprises a sensor 1 for detecting a light scattering intensity data with respect to (or concerning) a microcapsule in a medium; a central processing unit (CPU) 2 for responding to the light scattering intensity data obtained from the sensor 1 and conducting a series of processing in calculating the inner diameter of the microcapsule, the outer diameter thereof, and the wall thickness thereof and a printer 6 for outputting the calculated wall thickness of the microcapsule.

The central processing unit 2 comprises a memory circuit (or memory) 3 for storing a theoretical equation (or equation to be used in the calculation) for correlating at least a light scattering intensity characteristic with a particle size; and an arithmetic (or computing) circuit 5 for calculating the inner diameter and outer diameter based on the theoretical equation and the light scattering intensity data detected by the sensor 1, and calculating the wall thickness. Moreover, the central processing unit 2 comprises a control circuit 4 for controlling the data transfer between at least the memory circuit 3 and the arithmetic circuit 5 by following a predetermined program.

From the sensor 1, a light scattering intensity data I1 is given to the central processing unit 2 (S-1), (S-2), where the data I1 is measured with a microcapsule having a wall of a refractive index n1 dispersed in a medium.

The light scattering intensity data (or light scattering intensity characteristic, or scattering profile, hereinafter sometimes simply referred to as a light scattering intensity) I1 with respect to the inner diameter of the microcapsule can be obtained by measuring a light scattering intensity of a microcapsule dispersed in a medium 1 having the same refractive index n1 as that of the wall of the microcapsule. That is, if the refractive index of the medium 1 corresponds with that of the wall, the inner diameter of the microcapsule can be quasi-considered as the outer diameter thereof in the measurement of the light scattering intensity, thereby calculating as described below without a complicated theoretical equation.

Moreover, the measurement of the light scattering intensity for the microcapsule dispersed in a medium 2 having a refractive index n2 different from that of the wall (n2≠n1) can give a light scattering intensity data I2 with respect to the outer diameter of the microcapsule with the use of the refractive index difference (S-3). The data I2 is also sent to the central processing unit 2 (S-4).

Incidentally, the measurement sequence is not particularly limited to a specific one. The measurement in the medium 1 may be conducted first, or the measurement in the medium 2 may be conducted first.

The light scattering intensity data (I1, I2) may be manually or automatically fed into the central processing unit 2. Moreover, the light scattering intensity data from the sensor 1 may be sent to the central processing unit 2 after analog-to-digital conversion of the data with an analog-to-digital converter if necessary.

The light scattering intensity data (or light scattering intensity data with respect to the inner diameter and the outer diameter) I1 and I2 detected by the sensor 1 are stored in predetermined addresses of the memory circuit 3 constituting the central processing unit 2, respectively (S-5). Then, the stored data is fed to the arithmetic circuit 5, and the data is sent and received by the control circuit 4 between the arithmetic circuit 5 and the memory circuit 3 (S-6). The arithmetic circuit 5 calculates the inner diameter r1 and the outer diameter r2 from the theoretical equation based on each of the light scattering intensity data (S-7), and the data with respect to the calculated inner diameter r1 and the calculated outer diameter r2 are stored in predetermined addresses of the memory circuit 3, respectively (S-8). That is, the light scattering intensity data I1 (or light scattering intensity I2) detected by the sensor 1 is applied to the theoretical equation stored in the memory circuit 3, thereby the inner diameter r1 (or outer diameter r2) is calculated by the arithmetic circuit 5.

The theoretical equation (theoretical scattering intensity equation) to be stored in the memory circuit 3 is not particularly limited to a specific one if it is possible to correlate the light scattering intensity characteristic (particularly the intensity characteristic depending on a scattering angle) corresponding to the light scattering intensity data with the particle size. For example, a conventional theoretical equation for a spherical (or globular) particle may be used as the equation. The following shows a procedure for calculating an inner diameter (or outer diameter) by fitting (or matching) the light scattering intensity data I1 (or I2) to a theoretical equation for a spherical particle (any one of the following equations (1) to (4)).

The scattering intensity (scattering intensity for a spherical particle) I is equivalent to a theoretical scattering function S, and can be represented by the following theoretical equation (1).

$$I(q, r) = S(q, r) \quad (1)$$

$$S(q, r) = C \cdot \frac{9}{(qr)^6}[\sin(qr) - qr\cos(qr)]^2$$

$$q \equiv \frac{4\pi}{\lambda}\sin\left(\frac{\theta}{2}\right)$$

In the equation, "C" represents a shift factor, "r" represents a radius, "λ" represents a wavelength, and "θ" represents a scattering angle.

That is, in the above-mentioned equation (1), the inner diameter r1 (and outer diameter r2) can be obtained by a fitting (or matching) analysis correlating the theoretical scattering intensity I with the light scattering intensity data I1 (or I2) as an actually measured scattering intensity.

Moreover, the theoretical equation may consider interference effects between scattered particles. Since the influence of the interference between particles is usually reflected on the scattering intensity data, the consideration of the interference effects between scattered particles ensures more precise calculation of the inner diameter (and outer diameter). In the case considering the interference effects between scattered particles, an equation (the following equation (2)) in which the scattering function S in the equation (1) is replaced with a scattering function Sd based on Debye's hard sphere theory may be used.

$$I(q,r)=S_d(q,r)$$

$$S_d(q,r)=C[1-8vS(q,2r)]S(q,r) \quad (2)$$

In the equation, "v" represents a volume fraction of a particle, and "I", "r", "q", and "C" have the same meanings as defined above.

Moreover, the theoretical equation may consider a particle size distribution. Since the inner diameter (and outer diameter) of the microcapsule usually has a distribution in many cases, the inner diameter (and outer diameter) can be much more precisely calculated by taking account of the influence of the particle size distribution. The theoretical equation represented by the following equation (3) takes account of the particle size distribution with excluding the interference effects between scattered particles.

$$I(q, r) = C \int_0^\infty S(q, r)P(r)r^6 \, dr \quad (3)$$

$$\int_0^\infty P(r)dr = 1$$

In the equation, P(r) represents a particle size distribution function, and "I", "S", "r", "q", and "C" have the same meanings as defined above.

In the equation (3), the particle size distribution function P(r) includes a standardized function, for example, a standardized Gauss function.

In the theoretical equation, it is preferred that at least the particle size distribution is considered in order to calculate the inner diameter (and outer diameter) conforming to the substantial microcapsule. In particular, considering the interference effects between particles and the particle size distribution is preferred. That is, it is particulary preferred to fit the light scattering intensity data and a theoretical equation represented by the following equation (4), in which the interference effects between particles and the particle size distribution are considered.

$$I(q, r) = C \int_0^\infty S_d(q, r)P(r)r^6 \, dr \quad (4)$$

In the equation, "I", "Sd", "P", "r", "q", and "C" have the same meanings as defined above.

In such a fitting analysis, since the calculation of the inner diameter can be simplified by using a simple theoretical equation, a reliable data can be certainly obtained. Further, even when the interference effects between particles and the particle size distribution are considered, a theoretical equation can be established without complicating the equation, thereby ensuring a convenient and certain calculation of the inner diameter. In particular, consideration of the particle size distribution permits reliable calculation of the inner diameter or inner diameter distribution (or outer diameter or outer diameter distribution) conforming to the substance even in a polydisperse microcapsule.

Moreover, the outer diameter (or mean outer diameter) r2 of the microcapsule can be calculated by applying the light scattering intensity data I2 with respect to the outer diameter to the same equation as the light scattering intensity I1 (any one of the above-mentioned equations (1) to (4)) to fit the data to the equation by the same operation. Incidentally, since the intensity is measured in a medium having a refractive index n2 different from that having a refractive index n1, the outer diameter can be calculated independently of the species or diameter (or inner diameter) of the internal substance even by applying the above equation relative to the outer diameter.

The arithmetic circuit 5 further calculates (or computes) the wall thickness (or mean thickness) based on data with respect to the inner diameter r1 and outer diameter r2 (S–9). That is, the calculated inner diameter r1 and the calculated outer diameter r2 are stored in the predetermined addresses of the memory circuit 3, then the stored data is fed to the arithmetic circuit 5, and a data is sent and received by the control circuit 4 between the arithmetic circuit 5 and the memory circuit 3 to calculate a wall thickness (r2−r1) based on the inner diameter r1 and the outer diameter r2 by the arithmetic circuit 5.

The wall thickness (r2−r1) of the microcapsule calculated by the arithmetic circuit 5 responds to a drive signal from the control circuit 4 and is printed out from a printer 6 (S–10).

The wall thickness (r2−r1) of the microcapsule calculated by the arithmetic circuit 5 responds to a drive signal from the control circuit 4 and is printed out from a printer 6.

A detecting circuit as the detecting means is not particularly limited to a specific one as far as the circuit is measurable or detectable about a light scattering intensity or scattering profile of the microcapsule dispersed in the medium, and a conventional measuring apparatus may be used. Incidentally, in the measurement of the light scattering intensity, the wavelength of the irradiated light may be suitably selected depending on the outer diameter (or inner diameter) of the microcapsule, and is preferably selected in a wide range. For example, the wavelength may be about 100 to 3000 nm, preferably 200 to 2000 nm, and more preferably 300 to 1500 nm.

The memory means may be composed of a single memory circuit having various stored data, like the memory circuit 3, or may be composed of a plurality of memory circuits (e.g., both a memory circuit for storing a theoretical equation and an equation to be used in the calculation with respect to a thickness, and a memory circuit for storing calculation data such as an inner diameter and/or an outer diameter).

Moreover, in the memory means, a plurality of theoretical equations (e.g., the above-mentioned equations (3) and (4)) may be stored. In the case of storing a plurality of theoretical equations, a theoretical equation to be used may be selectively employed in accordance with an embodiment of the microcapsule (e.g., whether a microcapsule is a polydisperse one or not).

In the computing (or arithmetic means), the fitting analysis relative to the light scattering intensity data (or scattering profile) may be conducted by calculating the particle size distribution of the microcapsule. For example, on the basis of the light scattering intensity data (I1, I2) of the microcapsule (particularly, a polydisperse microcapsule), the inner diameter (or mean inner diameter), the outer diameter (or mean outer diameter), and the thickness (or mean thickness) may be computed (or calculated) as an inner diameter distribution P(r1), an outer diameter distribution P(r2), and a thickness distribution P(r2−r1), respectively. Further, both the individual calculation data (e.g., the mean thickness) and the distribution data (e.g., the thickness distribution) may be computed (or calculated) and may be able to be output.

The output means may be a display means (e.g., a display) without limited to the printer, as long as the wall thickness (r2−r1) can be output.

Incidentally, the present invention is available for a method for determining a wall thickness of a microcapsule. In this method, an apparatus using for the determination of the wall is not particularly limited to a specific one as long as light scattering characteristics (light scattering intensity data I1 and I2) are measurable as described above, and the above-mentioned apparatus may be suitably utilized.

According to the present invention, in the measurement of the light scattering intensity, the light scattering intensity data with respect to the inner diameter of the microcapsule can be obtained by corresponding or matching the refractive index of the microcapsule wall to the refractive index of the medium. That is, the matching can produce such a state that the internal substance of the microcapsule is dispersed in the medium as if there were not the wall. The light scattering intensity data with respect to the inner diameter can be obtained by measuring the light scattering intensity in such a state. Moreover, by applying a theoretical equation as the function of the microcapsule diameter (inner diameter or outer diameter) to the light scattering intensity data, the inner diameter can be calculated, further the wall thickness can be certainly calculated from the inner diameter and additionally the outer diameter which is calculated from the light scattering intensity data measured in the medium different in refractive index from the wall.

The microcapsule is not particularly limited to a specific one as long as the light scattering intensity is measurable, and may comprise a core substance (or internal substance) and a wall for covering (or protecting) the core substance. The configuration or shape (external configuration) of the microcapsule is not be limited to a specific one as long as the light scattering intensity is measurable, and is usually a spherical shape.

The microcapsule wall is not particularly limited to a specific one, and may be selected in accordance with the core substance quality (e.g., hydrophilicity, hydrophobicity). For example, the wall may comprise a polymer [e.g., a vinyl polymerization-series polymer such as a polyvinyl alcohol, a polystyrene, or an acrylic resin; a condensed polymer such as a polyamide, or a polyurethane], a cellulose derivative (e.g., an ethylcellulose), a protein (e.g., gelatin), and others.

The internal substance (core substance) of the microcapsule is not particularly limited to a specific form, and may be gaseous form, liquid form, or solid form. The internal substance may be a multicomponent system (e.g., a mixture of the internal substance with a plurality of different liquid components), or a form obtained by combining these forms (e.g., a disperse system of a liquid and a solid).

The material of the internal substance (core substance) is not particularly limited to a specific one, and includes, for example, a conventional core substance such as a liquid (e.g., a hydrocarbon such as toluene, an alcohol such as ethanol or glycerin, water), a plasticizer, a coloring agent (e.g., a pigment, a dye), a catalyst (e.g., an oxidant, a reducing agent, an initiator), a perfume material, a pharmaceutical, a biological material, a food (e.g., a flavor), a blowing agent, or an antirust.

It is sufficient that the overall configuration or shape of the internal substance may specify or determine the inner diameter, and the overall configuration or shape is usually a spherical configuration. Incidentally, it is enough that the refractive index of the internal substance may be different from that of the wall in a range calculable the wall thickness.

The inner diameter and the outer diameter of the microcapsule is not particularly limited to a specific one. The outer diameter may for example be about 0.1 μm to 1 mm, preferably about 1 to 100 μm, and the inner diameter may for example be about 0.05 μm to 0.99 mm, preferably about 0.5 to 99 μm.

The wall thickness of the microcapsule is not also limited to a specific one, and may be applied in a wide range (e.g., about 10 nm to 100 μm). In particular, since the light scattering intensity is measured in the medium such as a liquid without destruction of the microcapsule, the wall thickness can be accurately determined even in a relatively thin wall [for example, not more than 100 nm (e.g., about 10 to 100 nm), preferably not more than 50 nm (e.g., about 10 to 50 nm)].

Incidentally, the microcapsule may be a monodisperse microcapsule, or a polydisperse microcapsule as described above. Therefore, the inner diameter or the outer diameter may be calculated as a mean value (e.g., an arithmetic mean value), or calculated as a distribution (an inner diameter distribution, or an outer diameter distribution). In such a case, the wall thickness may be calculated as a mean thickness or a thickness distribution, according to the calculation method of the inner diameter or the outer diameter.

As the medium (medium 1 and 2), a liquid (a liquid insoluble to the microcapsule wall) is used in practical cases from a viewpoint of dispersing the microcapsule. The medium includes, in accordance with the quality (e.g., hydrophilicity, hydrophobicity) or refractive index of the wall, a transparent liquid, for example, an inorganic solvent (e.g., water, carbon disulfide), an organic solvent [for example, a hydrocarbon (e.g., an aliphatic hydrocarbon such as hexane, an alicyclic hydrocarbon such as cyclohexane, an aromatic hydrocarbon such as benzene or toluene), an alcohol (e.g., methanol, ethanol, ethylene glycol), an ether (e.g., diethyl ether, tetrahydrofuran), a ketone (e.g., acetone), an ester (e.g., ethyl acetate), a nitrile (e.g., acetonitrile), a halogen-containing solvent (e.g., a fluorine-containing solvent such as 1-fluoronaphthalene, a chlorine-containing solvent such as chloroform, a bromine-containing solvent such as bromobenzene or 1-bromonaphthalene, a iodine-containing solvent such as 1-iodonaphthalene or diiodomethane)], an oil (e.g., silicone oil), and others.

The liquid as the medium may comprise a single component, or a plurality of components as long as the plurality of components are miscible to each other and capable of maintaining transparency. In particular, in the case mixing a plurality of liquids, the medium 1 having the same refractive index as the microcapsule wall may be conveniently prepared. The refractive index of the medium mixture (particularly a mixed solvent) may be measured by a conventional refractometer (e.g., Abbe refractometer). The medium having a refractive index "n" may for example be prepared by mixing a liquid "A" having a refractive index "a" with a medium "B" having a refractive index "b" at a weight fraction "x" of the liquid "A", where the weight fraction "x" is determined to satisfy the following equation.

$$n = ax + b(1-x)$$

Incidentally, it is sufficient that the refractive index of the medium 1 may be substantially the same as the refractive index of the wall unless there is interference with the scattering intensity data with respect to the inner diameter. Moreover, it is enough that the refractive index of the medium 2 may be different from refractive index of the wall unless there is interference with the scattering intensity data with respect to the outer diameter. The difference between the refractive index n1 and n2 may be larger than the difference between the internal substance and the wall in refractive index, and may for example be not less than 0.01 (e.g., about 0.01 to 0.5, preferably about 0.1 to 0.5, and more preferably about 0.2 to 0.5).

According to the present invention, measuring a scattering intensity with matching a refractive index of a medium to be dispersed to a refractive index of a microcapsule wall ensures convenient and certain determination of the wall thickness of the microcapsule without destroying the wall. Moreover, even in a polydisperse microcapsule, the wall thickness of the microcapsule can be certainly determined.

INDUSTRIAL APPLICABILITY OF THE INVENTION

The present invention may be effectively utilized for determination of a wall thickness of a microcapsule. In particular, the present invention has a beneficial effect on determination for a wall thickness of a microcapsule having a particle size distribution and/or a thin wall.

What is claimed is:

1. An apparatus for determining a wall thickness of a microcapsule whose wall has a refractive index n1, comprising:

detecting means for detecting a light scattering intensity data I1 with respect to the microcapsule dispersed in a medium having a refractive index n1, and a light scattering intensity data I2 with respect to the microcapsule dispersed in a medium having a refractive index n2;

memory means for storing a theoretical equation for correlating a characteristic of a light scattering intensity with a particle size; and computing means for calculating an inner diameter r1 and an outer diameter r2 of the wall, from the theoretical equation based on the light scattering intensity data I1 and I2, and calculating a wall thickness (r2−r1).

2. An apparatus according to claim 1, wherein the characteristic of the light scattering intensity is an intensity characteristic depending on a scattering angle.

3. An apparatus according to claim 1, wherein a distribution P(r1) of the inner diameter and a distribution P(r2) of the outer diameter are calculated based on the light scattering intensity data I1 and I2 for a polydisperse microcapsule, and a wall thickness distribution P(r2−r1) is calculated.

4. An apparatus according to claim 1, wherein the difference between the refractive index n1 and the refractive index n2 is 0.01 to 0.5.

5. A method for determining a wall thickness of a microcapsule having a wall of a refractive index n1, comprising:

measuring a light scattering characteristic for the microcapsule dispersed in a medium having a refractive index n1 to provide a light scattering intensity data I1 followed by calculating an inner diameter r1 of the wall;

measuring a light scattering characteristic for the microcapsule dispersed in a medium having a refractive index n2 to provide a light scattering intensity data I2 followed by calculating an outer diameter r2 of the wall; and obtaining the wall thickness of the microcapsule based on a difference between the inner diameter r2 and the outer diameter r1, to determine the wall thickness of the microcapsule without destroying the wall.

6. The method according to claim 5, further comprising: outputting the calculated wall thickness.

* * * * *